United States Patent [19]

Hirai et al.

[11] 4,080,365
[45] Mar. 21, 1978

[54] PROCESS FOR PREPARING AROMATIC URETHANES

[75] Inventors: Yutaka Hirai; Katsuharu Miyata; Seiji Hasegawa, all of Omuta, Japan

[73] Assignee: Mitsui Toatsu Chemicals, Tokyo, Japan

[21] Appl. No.: 687,933

[22] Filed: May 19, 1976

[30] Foreign Application Priority Data

Jun. 17, 1975 Japan .................................. 50-72727

[51] Int. Cl.$^2$ .......................................... C07C 125/06
[52] U.S. Cl. ...................................... 560/25; 560/27; 560/28; 560/24; 560/12; 560/29; 560/30; 560/31; 560/32; 560/9
[58] Field of Search ................................. 260/471 C
[56] References Cited
U.S. PATENT DOCUMENTS 3,956,360  5/1976  Zajacek et al. ................. 260/471 C
3,993,685  11/1976 Zajacek et al. ................. 260/471 C Primary Examiner—Lorraine A. Weinberger
Assistant Examiner—Lisa Jones
Attorney, Agent, or Firm—Fisher, Christen & Sabol

[57] ABSTRACT

Aromatic urethanes can be produced in exceedingly improved yield when an aromatic nitro compound, an organic compound containing hydroxyl groups, and carbon monoxide are reacted in the presence of a catalyst composed of metallic (elemental) selenium or a selenium compound and a base serving as promoter, to which reaction system an aromatic amino compound and/or an aromatic urea compound which will be secondarily produced by the reaction has been previously added in order to suppress side reactions. For instance, when nitrobenzene, methanol and carbon monoxide are interacted in the presence of metallic selenium and triethylenediamine, the conversion of nitrobenzene is 68% and the percentage of formed methyl N-phenylcarbamate to the interacted nitrobenzene is 80%, whereas when the reaction is effected under the same reaction conditions indicated above with addition to the reaction system of aniline in an amount of about 15 wt. % of the nitrobenzene, the conversion of nitrobenzene and the percentage of formed methyl N-phenylcarbamate reach 100% and 98%, respectively.

9 Claims, No Drawings

PROCESS FOR PREPARING AROMATIC URETHANES

BACKGROUND OF THE INVENTION

1. Field of the Invention

This invention relates to a process for preparing an aromatic urethane (hereinafter referred to simply as urethane). More particularly, it relates to a process for preparing a urethane by interacting an aromatic nitro compound (hereinafter referred to simply as nitro compound), an alcohol and carbon monoxide in the presence of a selenium-containing catalyst.

2. Description of the Prior Art

Urethanes have been heretofore produced mainly by the reaction of isocyanates with alcohols. In recent years, the production of isocyanates has become difficult partly due to the lack and rising costs of starting materials therefor and partly due to high toxicity of intermediates when producing the isocyanates. As a result, there have been developed and proposed many novel processes for the production of urethanes without the use of isocyanates. However, these newly developed processes involve several serious problems and have not yet been reduced to practice on an industrial scale.

For example, U. S. Pat. No. 3,338,956 describes a process wherein urethanes are prepared from alcohols, carbon monoxide and nitro compounds by the use of a rhodium chlorocarbonyl catalyst. However, this process is economically disadvantageous in preparing highly pure urethane since urethanes are obtained only at low yield even when the urethanation reaction is effected by the use of a large amount of the catalyst over a long period of reaction time.

There has been further proposed a process in which urethanes are prepared by interacting hydroxyl group-containing organic compounds, carbon monoxide and nitro compounds in the presence of a catalyst composed of a carbonyl group-containing compound of a metal of Group VIII of the Periodic Table and coexisting with a promoter of a salt of a metal selected from those capable of existing in two or more valence states (German Pat. No. 1,543,051). However, this process is useless from an industrial point of view since the yield of urethane product is low even when mononitro compounds are used as starting material, whereas use of dinitro compounds as starting material results in an even lower yield.

Moreover, a process is known using palladium and a Lewis acid as catalyst (U.S. Pat. No. 3,531,512). In this process, urethanes are obtainable in some cases at a fairly high yield of 80%–90% even when dinitro compounds are used as starting material. In order to attain such high yield, however, it is necessary to effect the urethanation reaction under such severe reaction conditions as an initial carbon monoxide pressure of 190–350 kg/cm$^2$ and at a temperature of 190°–200° C. In addition, the process involves an industrially serious drawback that the Lewis acid, e.g., ferric chloride, used as promoter exerts a considerable corrosive action on metallic materials such as iron, stainless steel or the like. Accordingly, it is essential to use a reactor made of glass or tantalum so as to realize the process industrially. The use of a glass or tantalum reactor under the above-mentioned high temperature and pressure conditions, however, presents further technical and economical difficulties.

Further, French Pat. No. 2,197,862 describes a process using in combination selenium or a compound thereof and a base or water as catalyst. The reaction conditions of the process are milder than those of processes which have been previously known. However, the process undesirably involves side production of a substantial amount of amino compounds even if the reaction conditions are modified within defined ranges. Consequently, the yield of urethane becomes low. For example, so far as dinitrotoluene is concerned, the yield is at the best as low as 72–73%, higher yields being almost impossible to attain. As will be understood from the above, the process of the French Patent is not necessarily satisfactory for industrial production of urethanes. It will be noted that the mechanism of the urethanation reaction is not described in the French Patent specification. There is accordingly a strong demand for a process for preparing urethanes at higher yields.

SUMMARY OF THE INVENTION

It is therefore a primary object of the present invention to provide a novel process for preparing urethanes wherein the urethanes are obtained at exceedingly high yield without inducing any appreciable side reactions by interacting a nitro compound, an alcohol and carbon monoxide in the presence of a selenium-containing catalyst.

We have made an intensive study of urethanation reactions using a selenium-containing catalyst and found that the product obtained as a result of the urethanation reaction contains, apart from a main product of urethane, a substantial amount of side products such as aromatic amino compounds (hereinafter referred to simply as "amino compound(s)") formed from the starting nitro compound by conversion of the nitro groups of the nitro compound to amino groups or a mixture of amino groups and carbamate groups, and aromatic urea compounds (hereinafter referred to simply as "urea compound(s)") constituted of the amino compounds. Then, the urethanation reaction was effected by adding the above-mentioned by-products, i.e., amino compounds and urea compounds, to the starting mixture of the nitro compound, alcohol, carbon monoxide and catalyst. Surprisingly, it has been found that the resulting reaction product contains the amino and urea compounds only at about the same level as initially added. That is, conversion of the starting nitro compound into amino compounds is found to be suppressed, with the yield of urethane becoming almost quantitative on the basis of the starting nitro compound. The amino or urea compounds to be added to the starting mixture may be by-products which are obtained by separation and recovery from the reaction solution. Alternatively, as will be hereinafter described in detail, it may not be necessarily required to separate and recover the amino or urea compound from the reaction solution, i.e., there is also usable a mother liquor, per se, which contains the secondarily produced amino and urea compounds and which is obtained by removing part or most of the urethane product from the reaction solution by suitable means. The present invention is based on the above findings. It should be noted that the by-products formed by the urethanation reaction may contain a large proportion of amino compounds and only a small proportion of urea compounds, which proportions will vary depending on the kinds of starting nitro compounds and/or the reaction conditions. In this case, amino compounds alone will suffice to suppress the side amination reactions.

According to the present invention, there is provided a process for preparing an aromatic urethane which comprises interacting in the presence of a selenium-containing catalyst an aromatic nitro compound expressed by the following formula (1)

A—(NO$_2$)$_x$  (1)

wherein A represents a residue of an aromatic nitro compound from which nitro groups are removed, and $x$ is an integer of from 1 to 4, an alcohol expressed by the following formula (2)

R—OH  (2)

wherein R represents a linear or branched alkyl group containing from 1 to 16 carbon atoms, a cycloalkyl group having 6 carbon atoms with or without an alkyl substitutent containing from 1 to 3 carbon atoms, or an aralkyl group with an alkyl moiety containing from 1 to 6 carbon atoms, and carbon monoxide, and the improvement characterized by adding to the reaction system at least one compound selected from the group consisting of aromatic amino compounds expressed by the following formula (3)

(3)

wherein A and $x$ have the same meanings as defined in formula (1) for the aromatic nitro compound above, respectively, $y$ is an integer of from 1 to 4, $z$ is an integer of from 0 to 3, the total number of $y$ and $z$ not exceeding $x$, and R has the same meaning as defined in formula (2) for the alcohol above, and aromatic urea compounds expressed by following formula (4)

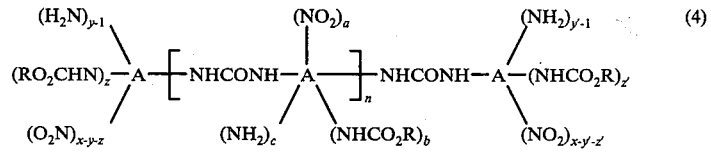

(4)

wherein A, R, $x$, $y$ and $z$ have the same meanings as defined in formulae (1), (2) and (3) above, respectively, $y'$ is an integer of from 1 to 4, $z'$ is an integer of from 0 to 3, the total number of $y'$ and $z'$ not exceeding $x$, all of $a$, $b$ and $c$ are 0 when $x = 1$ or 2, either one of $a$, $b$ or $c$ is 1 and the other two are 0 when $x = 3$, either one of $a$, $b$ or $c$ is 2 or any two among $a$, $b$ and $c$ are each 1 and the other is 0 when $x = 4$, $n$ is 0 when $x = 1$ and $n$ is an integer of from 0 to 3 when $x = 2 - 4$, whereby there can be obtained an aromatic urethane having the following formula (5)

A—(NHCO$_2$R)$_x$  (5)

wherein A, $x$ and R have the same meanings as defined in formulae (1) and (2) above, respectively, at high yield.

The reaction mechanism of the urethanation of the present invention is not completely understood at the present stage of our investigations. Since the reaction of formation of urethane from a nitro compound, carbon monoxide and an alcohol is not a so-called equilibrium reaction, it has not been expected that the side reactions can be suppressed when the urethanation reaction is carried out by adding to a starting reaction system compounds corresponding to the by-products as in the process of the present invention.

DESCRIPTION OF THE PREFERRED EMBODIMENTS

The aromatic nitro compounds useful as the main starting material in the present invention are those expressed by formula (1) above and may be nitrobenzene, dinitrobenzenes, dinitrotoluenes, nitronaphthalenes, nitroanthracenes, nitrobiphenyls, bis(nitrophenyl)alkanes, bis(nitrophenyl)ethers, bis(nitrophenyl)thioethers, bis(nitrophenyl)sulfons, nitrodiphenoxyalkanes, nitrophenothiazines and heterocyclic compounds such as 5-nitropyrimidine. Examples of suitable nitro compounds are nitrobenzene, o-, m- and p-nitrotoluene, o-nitro-p-xylene, 2-methyl-1-nitronaphthalene, m- and p-dinitrobenzene, 2,4- and 2,6-dinitrotoluene, dinitromesitylene, 4,4'-dinitrobiphenyl, 2,4-dinitrobiphenyl, 4,4'-dinitrodibenzyl, bis(4-nitrophenyl)methane, bis(4-nitrophenyl)-ether, bis(2,4-dinitrophenyl)ether, bis(4-nitrophenyl)thioether, bis(4-nitrophenyl)sulfon, bis(4-nitrophenoxy)ethane, α,α'-dinitro-p-xylene, α,α'-dinitro-m-xylene, 2,4,6-trinitrotoluene, o-, m- and p-chloronitrobenzene, 1-chloro-2,4-dinitrobenzene, 1-bromo-4-nitrobenzene, 1-fluoro-2,4-dinitrobenzene, o-, m- and p-nitrophenyl carbamate, o-, m- and p-nitroanisole, 2,4-dinitrophenetole, m-nitrobenzaldehyde, p-nitrobenzoyl chloride, ethyl-p-nitrobenzoate, m-nitrobenzenesulfonyl chloride, 3-nitrophthalic anhydride, 3,3'-dimethyl-4,4'-dinitrobiphenyl and the like, and isomers and homologues of these aromatic nitro compounds. These nitro compounds may be used singly or in combination. Among these, 2,4-dinitrotoluene and 2,6-dinitrotoluene are most preferred since the isocyanates obtained by thermal decomposition of the aromatic urethanes derived therefrom are very useful from an industrial viewpoint.

The alcohols suitable for the purpose of the invention are those expressed by formula (2) and may be any of a primary, a secondary and a tertiary alcohol. Examples of the alcohols include monohydric alcohols such as methyl alcohol, ethyl alcohol, n- and iso-propyl alcohol, n-, iso- and t-butyl alcohol, cyclohexyl alcohol, methylcyclohexyl alcohol, linear or branched amyl alcohol, hexyl alcohol, lauryl alcohol, cetyl alcohol, benzyl alcohol and the like. Of these, ethyl alcohol is preferred since useful isocyanates are obtainable by thermal decomposition of the aromatic urethanes derived from ethyl alcohol by the process of the present invention.

The alcohol may be generally used in the theoretical amount or greater, i.e., an amount equivalent to or greater than the chemical equivalence of nitro groups of the aromatic nitro compound. Preferably, the alcohol is employed in excess.

The aromatic amines usable in the present invention are those expressed by formula (3) and the choice of the aromatic amine depends upon the kind of nitro compound used as starting material. For example, when nitrobenzene is used as the nitro compound, aniline is suitable as the aromatic amine compound, while with nitrotoluene, aminotoluene is used. When dinitrobenzene is used as the nitro compound, nitroaniline, diaminobenzene and monocarbamate-monoaminobenzene are used as the aromatic amine compound. Further, use of dinitrotoluene as the nitro compound results in mononitromonoaminotoluene, diaminotoluene and monocarbamatemonoaminotoluene. Other amino compounds may be likewise exemplified if the aromatic nitro compound used as starting material is determined.

The aromatic urea compounds useful in the present invention are those expressed by formula (4) and the choice of the aromatic urea depends on the kind of starting nitro compound similarly as is the case with the aromatic amines. For example, when nitrobenzene is used as the nitro compound, 1,3-diphenylurea is suitably employed, and with nitrotoluene, 1,3-ditolylurea is used. With dinitrobenzene, various urea compounds are employable including 1,3-di(nitrophenyl)urea, 1,3-di(carbamatephenyl)urea, 1,3-di(aminophenyl)urea, 1-nitrophenyl-3-carbamatephenylurea, 1-nitrophenyl-3-aminophenylurea, 1-aminophenyl-3-carbamatephenylurea, and a polyurea compound containing as its constituting components nitroaniline, diaminobenzene or monocarbamatemonoaminobenzene, i.e., those expressed by the following formulae (6), (7), (8), (9), (10) or (11)

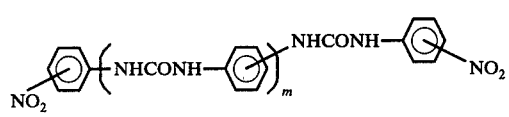

(6)

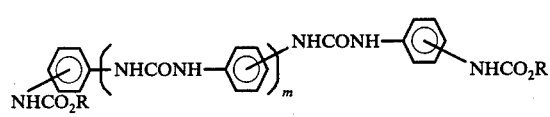

(7)

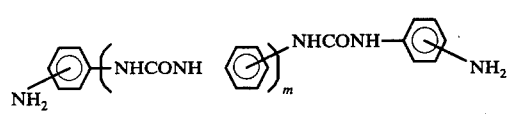

(8)

(9)

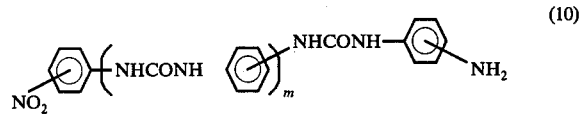

(10)

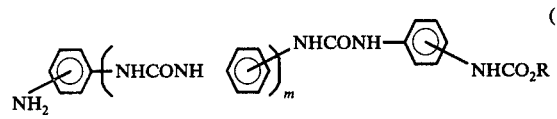

(11)

in which formulae (6), (7), (8), (9), (10) and (11) $m$ is independently an integer of from 1 to 3 and in which formulae (7), (9) and (11) R has independently the same meaning as defined in formula (2) above. When dinitrotoluene is used as the nitro compound, useful urea compounds are, for example, 1,3-di(nitrotolyl)-urea, 1,3-di(carbamatetolyl)urea, 1,3-di(aminotolyl)urea, 1-nitrotolyl-3-carbamatetolylurea, 1-nitrotolyl-3-aminotolylurea, 1-aminotolyl-3-carbamatetolylurea and a polyurea compound containing nitroaminotoluene, diaminotoluene or monocarbamatemonoaminotoluene as its constituting units. Other useful urea compounds corresponding to the respective starting aromatic nitro compounds may be similarly exemplified in accordance with formula (4).

In the practice of the invention, the urethanation reaction is effected by adding to the reaction system at least one compound selected from the group consisting of the aromatic amino compounds of formula (3) and the aromatic urea compounds of formula (4). The amount of the at least one compound will vary depending on the kind of starting aromatic nitro compound. If possible, the at least one compound is desirably employed in an amount substantially equal to the total amount of aromatic amino compound and urea compound which will be secondarily produced when no additives are used. For example, when nitrobenzene is used, it is sufficient to use aniline in an amount of 0.5–30 mole % and/or diphenylurea in an amount of 0.5–10 mole %, both based on the nitrobenzene (and, in the preferable case, aniline and diphenylurea are used in amounts of 5–15 mole % and 2–8 mole %, respectively). When 2,4-dinitrotoluene (and ethanol) are used as starting materials, an amino compound including 2-amino-4-nitrotoluene, 4-amino-2-nitrotoluene, 2-amino-4-ethylcarbamatetoluene, 4-amino-2-ethylcarbamatetoluene, 2,4-diaminotoluene or a mixture thereof in an amount of 1–20 mole % based on the 2,4-dinitrotoluene and/or a urea compound including 1,3-bis(3-nitro-4-methylphenyl)-urea, 1,3-bis(2-methyl-5-nitrophenyl)urea, 1,3-bis(3-ethylcarbamate-4-methylphenyl)urea, 1,3-bis(2-methyl-5-ethylcarbamatephenyl)urea, 1,3-bis(3-amino-4-methylphenyl)urea, 1,3-bis(2-methyl-5-aminophenyl)-urea, 1-(3-nitro-4-methylphenyl)-3-(2-methyl-5-nitrophenyl)urea, 1-(3-ethylcarbamate-4-methylphenyl)-3-(2-methyl-5-ethylcarbamatephenyl)urea, 1-(3-amino-4-methylphenyl)-3-(2-methyl-5-aminophenyl)-urea, 1-(3-nitro-4-methylphenyl)-3-(3-ethylcarbamate-4-methylphenyl)-urea, 1-(3-nitro-4-methylphenyl)-3-(2-methyl-5-ethylcarbamatephenyl)urea, 1-(3-nitro-4-methylphenyl)-3-(3-amino-4-methylphenyl)-urea, 1-(3-nitro-4-methylphenyl)-3-(2-methyl-5-aminophenyl)urea, 1-(2-methyl-5-nitrophenyl)-3-(3-ethylcarbamate-4-methylphenyl)urea, 1-(2-methyl-5-nitrophenyl)-3-(2-methyl-5-ethylcarbamatephenyl)urea, 1-(2-methyl-5-nitrophenyl-3-(3-amino-4-methylphenyl)urea, 1-(2-methyl-5-nitrophenyl)-3-(2-methyl-5-aminophenyl)urea, 1-(3-ethylcarbamate-4-methylphenyl)-3-(3-amino-4-methylphenyl)urea, 1-(3-ethylcarbamate-4-methylphenyl)-3-(2-methyl-5-aminophenyl)urea, 1-(2-methyl-5-ethylcarbamatephenyl)-3-(3-amino-4-methylphenyl)urea, 1-(2-methyl-5-ethylcarbamatephenyl)-3-(2-methyl-5-aminophenyl)urea, a polyurea compound having the afore-mentioned amino compound as its constituting units or a mixture thereof in an amount of 0.5–10 mole % based on the 2,4-dinitrotoluene is sufficiently used. Preferably, the amino compound and the urea compound are used, in combination, in amounts of 5–15 mole % and 2–8 mole %, respectively, based on the 2,4-dinitrotoluene.

Further, when 2,6-dinitrotoluene is used as the nitro compound (and ethanol as the alcohol), an amine compound such as 2-amino-6-nitrotoluene, 2-amino-6-ethylcarbamatetoluene, 2,6-di-aminotoluene or a mixture thereof is employed in an amount of 1–20 mole % based on the 2,6-dinitrotoluene and/or a urea compound such as 1,3-bis(2-methyl-3-nitrophenyl)urea, 1,3-bis(2-methyl-3-ethylcarbamatephenyl)urea, 1,3-bis(2-methyl-3-aminophenyl)urea, 1-(2-methyl-3-nitrophenyl)-3-(2-methyl-3-ethylcarbamatephenyl)urea, 1-(2-methyl-3-nitrophenyl)-3-(2-methyl-3-aminophenyl)urea, 1-(2-methyl-3-ethylcarbamatephenyl)-3-(2-methyl-3-aminophenyl)urea, a polyurea compound having therein the afore-said amino compound as constituting units thereof, or a mixture thereof in an amount of 0.5–10 mole % based on the 2,6-dinitrotoluene (and, preferably, the amino compound and the urea compound are used in combination in amounts of 5–15 mole % and 2–8 mole %, respectively, both based on the dinitrotoluene).

The amino compounds or urea compounds used in the present invention may be those which will be secondarily produced together with urethane in the urethanation reaction. In practical application, these by-products which have been separated and collected from the reaction solution may be used. Alternatively, a mother liquor which is obtained by removing part or most of the urethane product from the reaction solution by a suitable method may be used as it is.

In the reaction system of the present invention, a part of the added urea compound tends to be converted to a urethane and an amino compound in the presence of an alcohol under certain reaction conditions. Moreover, if an excess of an amino compound is added to the reaction system, a part of the amino compound reacts with urethane to form a urea compound, and if an amino compound and a urea compound are not present in the reaction system in amounts sufficient to suppress the side reactions, this lack will facilitate formation of by-products from the starting nitro compound. It will be noted that since the process of the present invention may involve collection and reuse of a reaction mother liquor which contains added or secondarily produced amino and urea compounds, the repeated use of the mother liquor by recirculation will naturally result in an optimum concentration of the amino and urea compounds even if these additives are not added in optimum amounts at an initial stage of the reaction. Accordingly, it is not necessarily required to add sufficient amounts of the additives to the reaction system from the beginning.

The urethanation reaction is carried out in the presence of a selenium-containing catalyst. The term "selenium-containing catalyst" as used herein is intended to mean a combination of metallic (elemental) selenium or a selenium compound and a base. The term "base" will be understood to imply an aliphatic, aralkyl or heterocyclic tertiary amine, or a metal salt of an carboxylic acid, sulfonic acid, phosphoric acid or phosphonic acid. Particular names and amounts of the bases are those described in detail in French Pat. No. 2,197,862, the teachings of which are incorporated herein by reference. Examples of suitable bases include pyridine, triethylamine, triethylenediamine, potassium acetate, sodium acetate and the like. The amount of the base is in the range of 2%–200% by weight of the starting nitro compound. The organic tertiary amine used in combination with the selenium or selenium compound must be distinguished in a strict sense from the aromatic amino compound which is employed for suppression of side production of amino compounds. This is because the organic tertiary amine constituting the catalyst together with the selenium or selenium compound has a remarkable effect on speeding the reaction but does not show any effect on suppression of side production of an aromatic amino compound from an aromatic nitro compound. In addition, the aromatic amino compound used in the process of the invention has no catalytic activity on the urethanation reaction when used along with selenium or a selenium compound.

Apart from the catalytic systems composed of selenium or a selenium compound and a base as described in French Pat. No. 2,197,862, we have found that a combination of selenium or a selenium compound with a salt of a bicyclic amidine and either a phenol or an organic carboxylic acid is very useful as the catalyst for the urethanation reaction. The bicyclic amidine is a compound expressed by the following formula (12)

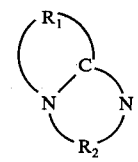

wherein $R_1$ and $R_2$ are independently a linear or branched alkylene group containing 2 or more carbon atoms or an alkylene group having a substituent which does not impede the urethanation reaction. Examples of the bicyclic amidines include 1,8-diazabicyclo(5,4,0)-undecene-7 (hereinafter referred to briefly as DBU), 1,5-diazabicyclo(4,3,0)-none-5 (hereinafter referred to briefly as DBN), etc. Examples of the phenols include phenol, o-, m- and p-cresol, o-, m- and p-xylenol, etc. The organic carboxylic acids are, for example, aliphatic carboxylic acids such as formic acid, acetic acid, propionic acid, oxalic acid, succinic acid, etc., and aromatic carboxylic acids such as benzoic acid, phthalic acid, hydroxybenzoic acid, etc. These organic carboxylic acids may contain a substituent not impeding the urethanation reaction, e.g., an alkyl group, a halogen, a cyano group or the like. In this instance, monochloroacetic acid, dichloroacetic acid, trichloroacetic acid, trifluoroacetic acid, monochloropropionic acid, cyanoacetic acid may be used as well as acetic acid.

The bicyclic amidine and the phenol or organic carboxylic acid may have been mixed with each other prior to use or may be separately added to the reaction system for mixing in the system. The phenol or carboxylic acid is used in an amount of 0.8–1.2 moles, preferably 1 mole, per mole of the bicyclic amidine. Use of bicyclic amidine or phenol or organic carboxylic acid alone gives no catalytic effect on the urethanation reaction. It is essential to use both in combination so as to produce the catalytic activity. Needless to say, the reaction does not proceed at all in the presence of selenium alone without use of the bicyclic amidine and the phenol or carboxylic acid. The amount of phenol or organic carboxylic acid salt of a bicyclic amidine is generally in the range of 1%–100% by weight, preferably 2%–50% by weight, of the nitro compound used. With greater amounts, the reaction proceeds more rapidly. Accordingly, more than 100% of the salt may be used but appears unnecessary in the general case. The advantage of the catalytic system is that high catalytic activity can be attained using only a small amount thereof. The organic amine, e.g., pyridine or triethylamine, used in French Pat. No. 2,197,862 shows hardly any catalytic activity when used in small amounts or even when used in combination with a phenol or an organic carboxylic acid. As will be understood from this fact, the catalytic system composed of selenium or a selenium compound and a salt of the bicyclic amidine and the phenol or organic carboxylic acid is a novel one which is completely different from those taught by the French Patent. This catalytic system and its use in the preparation of aromatic urethanes is disclosed in our copending application Ser. No. 664,995 filed Mar. 8, 1976.

Although French Pat. No. 2,197,862 describes use of water instead of a base, it is found desirable in the process of the present invention to remove water from the reaction system substantially completely. That is, though the increase of water content in the reaction system tends to make the reaction proceed more or less rapidly, a substantial amount of the produced urethane is decomposed by the water into the corresponding amino compound. The decomposition of a urethane into the corresponding amino compound cannot be suppressed by addition of an amino compound.

The selenium compounds useful in the urethanation reaction are those described in the French Patent. Examples of preferable selenium compounds include selenium dioxide, selenious acid, selenic acid, hydrogen selenide and carbonyl selenide. The amount of selenium or selenium compound is generally in the range of 0.1%–50% by weight, preferably 1%–20% by weight, of the starting nitro compound when calculated as elemental selenium.

The urethanation reaction may be effected in the absence of solvent since the alcohol serves as solvent but a solvent may be used. Examples of such solvent include aromatic solvents such as benzene, toluene, xylene, etc., nitriles such as acetonitrile, benzonitrile, etc., sulfones such as sulfolane, aliphatic halogenated hydrocarbons such as 1,1,2-trichloro-1,2,2-trifluoroethane, aromatic halogenated hydrocarbons such as monochlorobenzene, dichlorobenzene, trichlorobenzene, etc., ketones, esters, and other solvents such as tetrahydrofuran, 1,4-dioxane, 1,2-dimethoxyethane and the like.

The order of addition of the starting materials and catalyst is not limited and may be arbitrarily changed depending on the kind of apparatus used. For example, a starting mixture of alcohol, catalyst, amine and/or urea compound and organic nitro compound is introduced into a suitable pressure-resistant reactor such as an autoclave, into which carbon monoxide is further fed under pressure, followed by agitation under heating conditions until the urethanation reaction is completed. Carbon monoxide may be fed into the reactor either semi-continuously or continuously while discharging carbon dioxide produced as the reaction proceeds. The reaction may be carried out by a batch-wise, semi-continuous or continuous process. Carbon monoxide existing in excess after completion of the reaction may be reused by recirculation.

The reaction temperature is generally held in the range of 80°–220° C., preferably 120°–200° C. although the reaction proceeds more rapidly at higher reaction temperatures, a thermal decomposition tends to occur at temperatures above 220° C., lowering the yield of urethane product. The reaction pressure, i.e., the initial carbon monoxide pressure, is generally in the range of 10–300 kg/cm$^2$G, preferably 20–100 kg/cm$^2$G. The reaction time will depend upon the nature or kind of nitro compound used, the reaction temperature, reaction pressure, the kind and amount of catalyst and the kind of apparatus, but is generally in the range of 5 min. – 6 hours. After completion of the reaction, the reaction mixture is allowed to cool. After discharging the filled gas, the reaction mixture is subjected to a known separation such as filtration, distillation or other suitable method for separating the resulting urethane from unreacted materials, by-products, the solvent and catalyst.

In general, the urethane is separated as a precipitate when the reaction solution from which have been removed the insoluble matters such as catalyst is cooled. The reaction mother liquor obtained after separation of the urethane precipitate contains the amino compounds and urea compounds as well as non-precipitated urethane. By feeding back the mother liquor for reuse in a succeeding starting system, it becomes unnecessary to freshly add any amino and/or urea compounds to the reaction system. This mother liquor reusing method is very advantageous where the urethanation reaction is continuously conducted.

It has been found that the urea compound can be converted to the corresponding urethane and amino compounds by agitating in alcohol at a temperature of 160°–200° C. By this aftertreatment, the yield of urethane may be improved to a certain extent.

The process of the present invention has a remarkable advantage from an industrial point of view. That is, urethanes which have been hitherto produced only in low yield even under very severe reaction conditions with use of expensive catalysts can be obtained at almost theoretical or quantitative yield under mild conditions using inexpensive catalysts. The urethanes obtained by the process of the invention have wide utility as starting material for agricultural chemicals, isocyanates and polyurethanes.

The present invention will be particularly illustrated in the following examples, but is not intended to be limited thereto. In the examples, all of the reactions were effected in a stainless steel (SUS 32) autoclave of the electromagnetic agitation type. The conversions and yields shown in the examples were each calculated from the results of gas chromatography and liquid chromatography and expressed in terms of mole % based on starting nitro compound.

EXAMPLE 1

12.3 Grams of nitrobenzene, 1.75 grams of triethylenediamine, 1.0 grams of metallic selenium, 1.9 grams of aniline and 100 grams of methanol were introduced into an autoclave with an inner volume of 500 ml. The air in the autoclave was replaced by nitrogen gas and then carbon monoxide. Then, carbon monoxide was fed into the autoclave under pressure until the initial pressure reached 50 kg/cm$^2$G. When agitation was started and the temperature in the system was increased to 170° C., a pressure depression was recognized. The reaction system was agitated further at 170° C. for 20 min. As a result, no pressure depression was observed, the urethanation reaction being completed. The reaction solution was allowed to cool to room temperature and the gas in the reaction system was replaced by nitrogen. Then, the reaction solution was discharged from the autoclave. After separation of the solid selenium by filtration, the resulting filtrate was subjected to chromatographic analyses, revealing that no nitrobenzene was detected in the filtrate and that the filtrate contained 14.8 grams of urethane, i.e., methyl N-phenylcarbamate, 1.9 grams of aniline and 0.2 grams of 1,3-diphenylurea. The conversion of nitrobenzene was 100% and the yield of methyl N-phenylcarbamate was 98% based on the charged nitrobenzene. All of the charged aniline remained in the reaction solution.

COMPARATIVE EXAMPLE 1

Example 1 was repeated except that aniline was not used and the reaction was effected with agitation at a temperature of 170° C. for 30 min. The resultant reaction solution was subjected to chromatographic analyses, revealing that it contained 4.0 grams of nitrobenzene, 8.2 grams of methyl N-phenylcarbamate, 0.6 gram of aniline and 0.7 gram of 1,3-diphenylurea. The conversion of nitrobenzene was 68% and the yield of methyl N-phenylcarbamate based on the nitrobenzene was 80%. The percentages of formation of aniline and 1,3-diphenylurea were 10% and 5%, respectively. It will be understood by comparing these results with those of Example 1 that use of aniline together with the starting materials expedites the reaction and remarkably suppresses the conversion of nitrobenzene to aniline and 1,3-diphenyluea.

EXAMPLE 2

12.3 Grams of nitrobenzene, 1.5 grams of DBU, 0.6 gram of acetic acid, 0.5 gram of metallic selenium, 1.9 grams of aniline and 100 grams of ethanol were used for a urethanation reaction at a reaction temperature of 160° C. under an initial pressure of 70 kg/cm$^2$G in a manner similar to Example 1. The reaction was completed 20 min. after commencement thereof. As a result of analyses of the reaction solution, it was found that no nitrobenzene was detected and the solution contained 15.7 grams of ethyl N-phenylcarbamate, 2.0 grams of aniline, and 0.4 gram of 1,3-diphenylurea. The conversion of nitrobenzene was 100% and the yield of ethyl N-phenylcarbamate from nitrobenzene was 95%. The percentage of formation of aniline and 1,3-diphenylurea was 5%. When, after completion of the reaction, the reaction solution was agitated at 160°-180° C. for a further 30 min., 1,3-diphenylurea was reduced to a trace degree and the yield of ethyl N-phenylcarbamate was improved up to 97%.

EXAMPLE 3

Example 2 was repeated using 2.1 grams of 1,3-diphenylurea instead of aniline. The resulting reaction solution was subjected to the analyses, revealing that no nitrobenzene was detected and that it contained 16.4 grams of ethyl N-phenylcarbamate, 0.7 gram of aniline, and 1.5 grams of 1,3-diphenylurea. The conversion of nitrobenzene was 100% and the yield of ethyl N-phenylcarbamate from nitrobenzene was 99%. About 30% of the 1,3-diphenylurea charged together with the starting materials was decomposed into aniline and the N-phenylcarbamic acid ester. When the ethyl N-phenylcarbamate which was produced by decomposition of the charged 1,3-diphenylurea was subtracted from the yield, the total actual yield of ethyl N-phenylcarbamate was 96%. When compared with Comparative Example 1, it will be found that 1,3-diphenylurea used instead of aniline serves to suppress the formation of aniline from nitrobenzene.

EXAMPLE 4

18.1 Grams of 2,4-dinitrotoluene, 1.75 grams of triethylenediamine, 1.0 gram of metallic selenium, 2.0 grams of 2-amino-4-ethylcarbamatetoluene, 1.0 gram of 4-amino-2-ethylcarbamatetoluene 1.0 gram of a urea mixture of bis(2-methyl-4-ethylcarbamatephenyl)urea, bis(4-methyl-2-ethylcarbamatephenyl)urea and 1-(2-methyl-4-ethylcarbamatephenyl)-3-(4-methyl-2-ethylcarbamatephenyl)urea, and 100 grams of ethanol were used for reaction in a manner similar to Example 1 using an initial pressure of 70 kg/cm$^2$G, and a reaction temperature of 160° C–180° C. After 40 min., the reaction was completed. The reaction solution was subjected to the analyses, revealing that no 2,4-dinitrotoluene was detected and that it contained 2.4 grams of 2-amino-4-ethylcarbamatetoluene, 1.0 gram of 4-amino-2-ethylcarbamatetoluene, 26.0 grams of diethylcarbamatetoluene and 1.0 gram of the urea compound. From the results, it will be understood that the conversion of dinitrotoluene was 100%, the yield of 2,4-dicarbamatetoluene was 98%, and the side reactions for formation of the amino compound and urea compound from dinitrotoluene were almost completely suppressed.

COMPARATIVE EXAMPLE 2

18.1 Grams of 2,4-dinitrotoluene, 1.75 grams of triethylenediamine, 1.0 gram of metallic selenium and 100 grams of ethanol were reacted similarly to Example 4 without use of either 2-amino-4-ethylcarbamatetoluene or the urea compound at a reaction temperature of 160° C. under an initial carbon monoxide pressure of 70 kg/cm$^2$G. The reaction was completed 110 min. after commencement thereof. The resulting reaction solution was subjected to chromatographic analyses, revealing that no 2,4-dinitrotoluene was detected and it contained 2.0 grams of 2-amino-4-ethylcarbamatetoluene, 1.0 gram of 4-amino-2-ethylcarbamatetoluene, 21.8 grams of diethylcarbamatetoluene (i.e., bisurethane) and 1.0 gram of a urea compound. The yield of 2,4-diethylcarbamatetoluene from the 2,4-dinitrotoluene was 82% and the percentage of side production of the amino carbamate and urea compounds was 18%.

EXAMPLE 5

A reaction solution obtained similarly to Comparative Example 2 was subjected to distillation under reduced pressure for removing ethanol therefrom, followed by condensing and evaporating to dryness. The dried matter was then dissolved in chloroform and extracted with dilute hydrochloric acid to separate the contained amino compound in the form of a hydrochloric acid salt. The dilute hydrochloric acid phase or layer was neutralized with sodium hydroxide and extracted with chloroform. Thereafter, the chloroform was removed by distillation from the chloroform layer to obtain about 3.0 grams of a free amino compound. 3.0 Grams of this amino compound which was a by-product thus collected from the reaction solution was used together with 18.1 grams of 2,4-dinitrotoluene, 1.75 grams of diethylenediamine, 1.0 gram of selenium and 100 grams of ethanol for reaction in the same manner as in Example 4. The reaction was completed 60 min. after commencement thereof. The resulting reaction solution was subjected to chromatographic analyses, revealing that the conversion of 2,4-dinitrotoluene was 100%, the yield of 2,4-diethylcarbamatetoluene from the charged 2,4-dinitrotoluene was 95%, and the total percentage of side production of an amino compound and a urea compound was 5%.

EXAMPLE 6

A solution as obtained in Example 4 was filtered to separate the solid selenium therefrom. The resulting filtrate was cooled to 10° C. to obtain 16.8 grams of crystals of diethylcarbamatetoluene having a purity of 95% and containing 3% of 2-amino-4-ethylcarbamatetoluene and 2% of a urea compound. To the filtrate, from which the crystals had been removed, were added 18.1 grams of 2,4-dinitrotoluene, 0.5 gram of selenium and 10 grams of ethanol for reaction in the same manner as in Example 4. After 40 min., the reaction was completed. Then, the solid selenium was separated, similarly to Example 4, from the resulting reaction solution, which was cooled to obtain 25.8 grams of crystal diethylcarbamatetoluene having a purity of 97% and containing 2% of 2-aminocarbamatetoluene and 1% of a urea compound. The crystals were removed from the reaction solution. To the filtrate were again added 18.1 grams of 2,4-dinitrotoluene, 0.5 gram of selenium and 20 grams of ethanol for further reaction. The reaction was completed 50 min. after commencement thereof. The resulting reaction solution was cooled to obtain 26.5 grams of crystal 2,4-diethylcarbamatetoluene having a purity of 98% and containing 2% of 2-amino-4-ethylcarbamatetoluene and a trace of a urea compound. The resulting filtrate was subjected to chromatographic analyses, revealing that the filtrate contained 10.6 grams of 2,4-diethylcarbamatetoluene, 2.0 grams of 2-amino-4-ethylcarbamatetoluene, 1.0 gram of 4-amino-2-ethylcarbamatetoluene and 0.7 gram of a urea compound. From the above results, it will be understood that the repeated use of a reaction mother liquor by recirculation is effective in continuously producing diethylcarbamatetoluene at high yield.

EXAMPLE 7

18.1 grams of 2,4-dinitrotoluene, 0.5 gram of potassium acetate, 3.0 grams of 2-amino-4-ethylcarbamatetoluene, 1.0 gram of 4-amino-2-ethylcarbamatetoluene, 1.0 gram of selenium and 100 grams of ethanol were used for reaction in the same manner as in Example 4. The reaction was completed 40 min. after commencement of the reaction. The resulting reaction solution was subjected to chromatographic analyses, revealing that it contained 25.8 grams of 2,4-diethylcarbamatetoluene, 2.4 grams of 2-amino-4-ethylcarbamatetoluene, 1.2 grams of 4-amino-2-ethylcarbamatetoluene and a trace of a urea compound. The conversion of 2,4-dinitrotoluene was 100%, the yield of 2,4-diethylcarbamatetoluene was 97%, and the percentage of side production of aminocarbamate was 3%.

The above process was repeated using sodium acetate instead of potassium carbamate. 40 Min. after commencement of the reaction, the conversion of 2,4-dinitrotoluene reached 100%, the yield of 2,4-diethylcarbamatetoluene was 91%, and the precentage of side production of aminocarbamate was 9%.

EXAMPLE 8

Example 7 was repeated using 2.0 grams of 2-amino-4-nitrotoluene and 1.0 gram of 4-amino-2-nitrotoluene instead of the 2-amino-4-ethylcarbamatetoluene and 4-amino-2-ethylcarbamatetoluene, respectively. The reaction was completed after 40 min. The resulting reaction solution was subjected to chromatographic analyses, revealing that there were contained 25.5 grams of 2,4-diethylcarbamatetoluene, 2.6 grams of 2-amino-4-ethylcarbamatetoluene, 1.6 grams of 4-amino-2-ethylcarbamatetoluene and 0.8 gram of a urea compound. The yield of 2,4-diethylcarbamatetoluene from 2,4-dinitrotoluene was 96%. Most of the aminonitrotoluene added together with the starting materials was converted to the aminocarbamatetoluene and the urea compound.

EXAMPLE 9

Example 4 was repeated using 18.1 grams of 2,6-dinitrotoluene, 0.5 gram of potassium acetate, 2.0 grams of 2-amino-6-ethylcarbamatetoluene, 1.0 gram of selenium and 100 grams of ethanol. The reaction was completed 60 min. after commencement of the reaction. The resulting reaction solution was subjected to chromatographic analyses, revealing that there were contained in the solution 25.6 grams of 2,6-diethylcarbamatetoluene, 3.8 grams of 2-amino-6-ethylcarbamatetoluene, and only a trace of a urea compound. The yield of 2,6-dicarbamatetoluene was 96% and the percentage of side production of the aminocarbamate was 4%.

COMPARATIVE EXAMPLE 3

Example 9 was repeated without use of 2-amino-6-ethylcarbamatetoluene. As a result, the yield of 2,6-diethylcarbamatetoluene from 2,6-dinitrotoluene was reduced down to 85% and the percentage of side production of 2-amino-6-ethylcarbamatetoluene was 15%.

What is claimed is:

1. In a process for preparing an aromatic urethane which comprises interacting an aromatic nitro compound expressed by formula (1)

$$A—(NO_2)_x \qquad (1)$$

wherein A represents the residue of an aromatic nitro compound from which nitro groups are removed, and $x$ is an integer of from 1 to 4, an alcohol expressed by formula (2)

$$R—OH \qquad (2)$$

wherein R represents a linear or branched alkyl group containing from 1 to 16 carbon atoms, a cycloalkyl group having 6 carbon atoms with or without an alkyl substituent containing from 1 to 3 carbon atoms, or an aralkyl group having an alkyl moiety containing from 1 to 6 carbon atoms, and carbon monoxide in the presence of a selenium-containing catalytic system, the improvement which comprises adding to the reaction system at least one compound selected from the group consisting of an aromatic amino compound expressed by formula (3)

wherein A and $x$ have the same meanings as defined in formula (1), respectively, $y$ is an integer of from 1 to 4, $z$ is an integer of from 0 to 3, the total number of $y$ and $z$ not exceeding $x$, and R has the same meaning as defined in formula (2) and aromatic urea compounds expressed by formula (4)

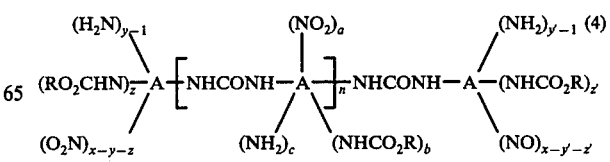

wherein A and $x$, R, and $y$ and $z$ have, respectively, the same meanings as defined in formulae (1), (2) and (3), $y'$ is an integer of from 1 to 4, $z'$ is an integer of from 0 to 3, the total number of $y'$ and $z'$ not exceeding $x$, and $a$, $b$ and $c$ are each 0 when $x = 1$ or 2, one of $a$, $b$ or $c$ is 1 and the other two is 0 when $x = 3$, one of $a$, $b$ or $c$ is 2 and the other two are 0 or any two of $a$, $b$ and $c$ are 1 and the other is 0 when $x = 4$, and $n$ is 0 when $x = 1$ and $n$ is an integer of from 0 to 3 when $x = 2 - 4$, whereby there is obtained at high yield an aromatic urethane expressed by formula (5)

wherein A and $x$ have the same meanings as defined in formula (1), respectively, and R as defined in formula (2).

2. The process according to claim 1 wherein said aromatic nitro compound expressed by formula (1) is dinitrotoluene.

3. The process according to claim 1, wherein said alcohol expressed by formula (2) is ethyl alcohol.

4. The process according to claim 1, wherein said aromatic nitro compound expressed by formula (1) is 2,4-dinitrotoluene, said alcohol expressed by formula (2) is ethyl alcohol, and said aromatic amino compound expressed by formula (3) is a member selected from the group consisting of 2-amino-4-ethylcarbamatetoluene, 4-amino-2-ethylcarbamatetoluene, 2-amino-4-nitrotoluene, 4-amino-2-nitrotoluene and 2,4-diaminotoluene.

5. The process according to claim 1, wherein said aromatic nitro compound expressed by formula (1) is 2,6-dinitrotoluene, said alcohol expressed by formula (2) is ethyl alcohol, and said aromatic amino compound expressed by formula (3) is a compound selected from the group consisting of 2-amino-6-nitrotoluene, 2-amino-6-ethylcarbamatetoluene and 2,6-diaminotoluene.

6. The process according to claim 1, wherein said aromatic nitro compound expressed by formula (1) is 2,4-dinitrotoluene, said alcohol expressed by formula (2) is ethyl alcohol, and said aromatic urea compound expressed by formula (4) is at least one compound selected from the group consisting of 1,3-bis(3-nitro-4-methylphenyl)urea, 1,3-bis-(2-methyl-5-nitrophenyl)urea, 1,3-bis(3-ethylcarbamate-4-methylphenyl)urea, 1,3-bis(2-methyl-5-ethylcarbamatephenyl)urea, 1,3-bis(3-amino-4-methylphenyl)urea, 1,3-bis(2-methyl-5-aminophenyl)urea, 1-(3-nitro-4-methylphenyl)-3-(2-methyl-5-nitrophenyl)urea, 1-(3-ethylcarbamate-4-methylphenyl)-3-(2-methyl-5-ethylcarbamatephenyl)urea, 1-(3-amino-4-methylphenyl)-3-(2-methyl-5-aminophenyl)urea, 1-(3-nitro-4-methylphenyl)-3-(3-ethylcarbamate-4-methylphenyl)urea, 1-(3-nitro-4-methylphenyl)-3-(2-methyl-5-ethylcarbamatephenyl)urea, 1-(3-nitro-4-methylphenyl)-3-(3-amino-4-methylphenyl)urea, 1-(3-nitro-4-methylphenyl)-3-(2-methyl-5-aminophenyl)urea, 1-(2-methyl-5-nitrophenyl)-3-(3-ethylcarbamate-4-methylphenyl)urea, 1-(2-methyl-5-nitrophenyl)-3-(2-methyl-5-ethylcarbamatephenyl)urea, 1-(2-methyl-5-nitrophenyl)-3-(3-amino-4-methylphenyl)urea, 1-(2-methyl-5-nitrophenyl)-3-(2-methyl-5-aminophenyl)urea, 1-(3-ethylcarbamate-4-methylphenyl)-3-(3-amino-4-methylphenyl)urea, 1-(3-ethylcarbamate-4-methylphenyl-3-(2-methyl-5-aminophenyl urea, 1-(2-methyl-5-ethylcarbamatephenyl)-3-(3-amino-4-methylphenyl)urea and 1-(2-methyl-5-ethylcarbamatephenyl)-3-(2-methyl-5-aminophenyl)urea.

7. The process according to claim 1, wherein said aromatic nitro compound expressed by formula (1) is 2,6-dinitrotoluene, said alcohol expressed by formula (2) is ethyl alcohol, and said aromatic urea compound expressed by formula (4) is at least one compound selected from the group consisting of 1,3-bis(2-methyl-3-nitrophenyl)urea, 1,3-bis(2-methyl-3-ethylcarbamatephenyl)urea, 1,3-bis(2-methyl-3-aminophenyl)urea, 1-(2-methyl-3-nitrophenyl-3-(2-methyl-3-ethylcarbamatephenyl)urea, 1-(2-methyl-3-nitrophenyl)-3-(2-methyl-3-aminophenyl)urea, and 1-(2-methyl-3-ethylcarbamatephenyl)-3-(2-methyl-3-aminophenyl urea.

8. The process according to claim 1, wherein said selenium-containing catalytic system is composed of (a) a catalyst selected from the group consisting of elemental selenium and selenium dioxide and (b) a promoter selected from the group consisting of potassium acetate, sodium acetate and triethylenediamine.

9. The process according to claim 1, wherein said selenium-containing catalytic system is composed of (a) a catalyst selected from the group consisting of elemental selenium and selenium dioxide and (b) a promoter consisting of 1,8-diazabicyclo (5,4,0)-undecene-7 and acetic acid.

* * * * *